United States Patent [19]

Bowman

[11] Patent Number: 4,668,434
[45] Date of Patent: May 26, 1987

[54] PET SHAMPOO
[75] Inventor: Hal K. Bowman, Cary, N.C.
[73] Assignee: Zema Corporation, Raleigh, N.C.
[21] Appl. No.: 815,374
[22] Filed: Dec. 31, 1985
[51] Int. Cl.$^4$ ............................................. A61K 2/46
[52] U.S. Cl. ................................ 252/522 A; 119/1;
424/70; 424/DIG. 10; 252/174.11
[58] Field of Search ................ 526/263; 252/522 A,
252/174.11; 119/1; 424/DIG. 10, DIG. 13, 70

[56] References Cited
U.S. PATENT DOCUMENTS

| | | | |
|---|---|---|---|
| 3,567,118 | 3/1971 | Shepherd et al. | 252/522 A |
| 3,772,215 | 11/1973 | Gould et al. | 252/522 A |
| 3,775,227 | 11/1973 | Wilbert et al. | 252/522 A |
| 3,806,317 | 4/1974 | Viout et al. | 526/263 |
| 3,939,099 | 2/1976 | Tusa et al. | 252/522 A |
| 3,966,902 | 6/1976 | Chromecek | 424/DIG. 10 |
| 3,990,459 | 11/1976 | Papantoniou | 526/263 |
| 4,036,788 | 7/1977 | Steckler | 526/263 |
| 4,209,417 | 6/1980 | Whyte | 252/522 A |
| 4,339,356 | 7/1982 | Whyte | 252/522 A |
| 4,492,644 | 1/1985 | Matsumoto et al. | 252/522 A |
| 4,540,721 | 9/1985 | Staller | 252/522 A |

Primary Examiner—James H. Reamer
Attorney, Agent, or Firm—Ernest V. Linek; Donald Brown

[57] ABSTRACT

The present invention is directed to a composition of matter which provides a slow release fragrance for animal skin products such as shampoos, conditioners, insect (e.g., flea, tick) repellants or insecticides.

The present invention is especially directed to the use of a combination of one or more perfumes and a polymer that, when added to hair coat treatment products for animals, extend the aromatic life of the fragrance.

Preferably, the slow release fragrance composition comprises a fragrance base, such as any of the commercially available perfumes or perfume concentrates, and a water-soluble polymer. Preferably, the polymer is a vinyl copolymer. The most preferred polymer is the copolymer obtained by reaction of the monomers N-vinylpyrrolidone and dimethylamino ethyl methacrylate.

18 Claims, No Drawings

PET SHAMPOO

BACKGROUND OF THE INVENTION

It has long been evident that animal owners applying shampoos, conditioners, repellents or insecticides to their animal's coat desire a long-lasting fragrance to mask normal animal odors. Most animal skin application products contain standard cosmetic fragrances that rapidly vaporize and therefore mask the normal animal odors for only a few hours. A non-toxic, slow release system that may conveniently be added to most animal skin application products would be a highly desirable goal. This invention accomplishes that goal by pre-mixing a commercial fragrance base with a vinyl copolymer.

SUMMARY OF THE INVENTION

The present invention is directed to a composition of matter which provides a slow release fragrance for animal skin products such as shampoos, conditioners, insect (e.g., flea, tick) repellants or insecticides.

The present invention is especially directed to the use of a combination of one or more perfumes and a vinyl copolymer that, when added to hair coat treatment products for animals, extend the aromatic life of the fragrance.

DETAILED DESCRIPTION OF THE PREFERRED EMBODIMENTS

Generally, animal shampoos consist of an aqueous solution, emulsion, or dispersion of one or more cleansing agents, together with additives employed for the purposes of modifying and stabilizing the various functional and aesthetic properties of the finished product. Additives include solubilizers, foam modifiers, dispersants, conditioning agents, medicaments, pH controls, preservative systems, and the like.

The present invention incorporates within such a shampoo formulation, a slow release fragrance composition. Preferably, the slow release fragrance composition comprises a fragrance base, such as any of the commercially available perfumes or perfume concentrates, and a water-soluble polymer. Preferably, the polymer is a vinyl copolymer. The most preferred polymer is the copolymer obtained by reaction of the monomers N-vinylpyrrolidone and dimethylamino ethyl methacrylate.

Depending upon the fragrance requirements, the fragrance base may be admixed with the copolymer in amounts varying from about 1 weight percent to about 50 weight percent. Preferably, the fragrance is admixed with the polymer in a weight ratio of about 1 to 4. A preferred fragrance base is available from Roure Bertrand Dupont, Inc. of 1775 Windsor Road, Teaneck, N.J. 07666, under the designation Q-1782.

The slow release fragrance composition of the present invention is not limited to use in shampoo products. Other pet products may likewise be treated as herein described. Such other products which may benefit from incorporation of an extended life fragrance include conditioners, insect repellants and/or insecticide products.

EXAMPLE

A mixture of Roure Bertrand Dupont, Inc. perfume concentrate Q-1782 is mixed with vinyl pyrrolidone/-dimethylamino ethyl methacrylate copolymer in a weight ratio of 1:4. This fragrance combination is then formulated with the basic ingredients of shampoo, conditioner, repellent or insecticide products. The amount of fragrance combination added to the basic pet product ingredients may be varied depending upon the strength of the fragrance desired. Generally, the fragrance combination is present in at least about 0.1 wt. percent of the basic ingredients, preferably in at least about 0.5 weight percent.

The present invention has been described in detail, including the preferred embodiment thereof. However, it will be appreciated that those skilled in the art, upon consideration of the present invention disclosure, may make modifications and/or improvements on this invention and still be within the scope and spirit of this invention as set forth in the following claims.

What is claimed is:

1. A slow release fragrance composition, suitable for use in animal hair coat treatment products consisting essentially of an intimate admixture of a fragrance base and a water soluble vinyl polymer, said fragrance base being present in said admixture at from about 1 to 50 weight percent, said composition being able to impart a long-lasting fragrance to the animal coat.

2. The slow release composition of claim 1, wherein said vinyl polymer is a copolymer of N-vinyl pyrrolidone and dimethylamino ethyl methacrylate.

3. The slow release composition of claim 2, wherein said fragrance base is a perfume.

4. The slow release composition of claim 3, wherein said perfume is Q-1782.

5. The slow release composition of claim 1, further comprising ingredients suitable for use as a shampoo.

6. The slow release composition of claim 1, further comprising ingredients suitable for use as a conditioner.

7. The slow release composition of claim 1, further comprising ingredients suitable for use as an insect repellant.

8. The slow release composition of claim 1, further comprising ingredients suitable for use as an insecticide.

9. A method of imparting a long lasting fragrance to the coat of animals comprising applying to said coat a shampoo formulation containing the slow release composition of claim 1.

10. A method of imparting a long lasting fragrance to the coat of animals comprising applying to said coat a conditioner formulation containing the slow release composition of claim 1.

11. A method of imparting a long lasting fragrance to the coat of animals comprising applying to said coat an insect repellant formulation containing the slow release composition of claim 1.

12. A method of imparting a long lasting fragrance to the coat of animals comprising applying to said coat an insecticide formulation containing the slow release composition of claim 1.

13. An animal coat treated with a formulation containing the slow release composition of claim 1.

14. The method of extending the aromatic fragrance life of a perfume used in hair coat treatment products for animals comprising mixing the perfume with a vinyl copolymer.

15. In an animal shampoo formulation containing one or more cleansing agents, solubilizers, stabilizers, foam modifiers, dispersants, pH controls, and preservative agents;

the improvement comprising;

adding an effective amount of a long-lasting perfume composition to said shampoo formulation, said perfume composition consisting essentially of a perfume concentrate and a vinyl pyrrolidone-dimethylamino ethylmethacrylate copolymer in a weight ratio of 1:4.

16. The improved animal shampoo of claim 15, which further includes an effective amount of insect repellant and/or insecticide.

17. In an animal coat conditioner formulation containing one or more conditioning agents, solubilizers, stabilizers, foam modifiers, dispersants, pH controls, and preservative agents;

the improvement comprising;

adding an effective amount of a long-lasting perfume composition to said conditioner formulation, said perfume composition consisting essentially of a perfume concentrate and a vinyl pyrrolidone-dimethylamino ethylmethacrylate copolymer in a weight ratio of 1:4.

18. The improved animal coat conditioner of claim 17, which further includes an effective amount of insect repellant and/or insecticide.

* * * * *